(12) United States Patent
Bara

(10) Patent No.: US 7,696,147 B2
(45) Date of Patent: Apr. 13, 2010

(54) PERFUME COMPOSITION

(75) Inventor: Isabelle Bara, La Varenne-St-Hilaire (FR)

(73) Assignee: L'Oreal, Paris (FR)

( * ) Notice: Subject to any disclaimer, the term of this patent is extended or adjusted under 35 U.S.C. 154(b) by 896 days.

(21) Appl. No.: 10/563,967

(22) PCT Filed: Jun. 24, 2004

(86) PCT No.: PCT/EP2004/006902

§ 371 (c)(1),
(2), (4) Date: Jan. 6, 2006

(87) PCT Pub. No.: WO2005/004828

PCT Pub. Date: Jan. 20, 2005

(65) Prior Publication Data

US 2006/0178290 A1    Aug. 10, 2006

Related U.S. Application Data

(60) Provisional application No. 60/490,255, filed on Jul. 28, 2003.

(30) Foreign Application Priority Data

Jul. 8, 2003    (FR) .................... 03 08323

(51) Int. Cl.
*A61K 8/00* (2006.01)
*B65D 83/14* (2006.01)
*A61Q 13/00* (2006.01)
*A61K 8/18* (2006.01)

(52) U.S. Cl. .......................... 512/1; 222/635
(58) Field of Classification Search .......... 512/1; 516/8; 222/635
See application file for complete search history.

(56) References Cited

U.S. PATENT DOCUMENTS

| | | | | | |
|---|---|---|---|---|---|
| 5,013,763 | A | * | 5/1991 | Tubesing et al. | 514/772 |
| 5,160,494 | A | * | 11/1992 | Krzysik et al. | 512/3 |
| 5,288,482 | A | * | 2/1994 | Krzysik | 424/64 |
| 5,670,159 | A | * | 9/1997 | Morton et al. | 424/401 |
| 6,013,683 | A | * | 1/2000 | Hill et al. | 516/67 |
| 6,395,704 | B1 | * | 5/2002 | Branlard et al. | 512/1 |
| 6,432,912 | B1 | * | 8/2002 | Rodelet | 512/1 |

FOREIGN PATENT DOCUMENTS

| | | |
|---|---|---|
| DE | 43 41 652 | 6/1994 |
| EP | 0 527 496 | 2/1993 |
| EP | 0 566 240 | 10/1993 |
| FR | 2 791 886 | 10/2000 |
| WO | 99/06017 | 2/1999 |
| WO | 01/00141 | 1/2001 |

OTHER PUBLICATIONS

Dow Corning Corporation MSDS Dow Corning 200® Fluid 0.65 /cst Aug. 28, 2008 p. 2.*
Dow Corning Corporation Formulation Information "All Day Perfume Gel" Mar. 1, 2004 p. 1.*
Dow Corning Corporation MSDS Dow Corning OS-20 Aug. 1, 2001 p. 1.*
Dow Corning Corporation MSDS Dow Corning OS-2 Sep. 12, 2008 p. 2.*

* cited by examiner

*Primary Examiner*—James Seidleck
*Assistant Examiner*—Aaron Greso
(74) *Attorney, Agent, or Firm*—Oblon, Spivak, McClelland, Maier & Neustadt, L.L.P.

(57) ABSTRACT

The present invention relates to a perfume composition comprising a mixture of fragrant materials in a physiologically acceptable carrier comprising a mixture of polydimethylsiloxanes, characterized in that the said mixture of polydimethylsiloxanes consists of hexamethyldisiloxane and octamethyltrisiloxane, in a weight ratio of between 30:70 and 70:30.

15 Claims, No Drawings

PERFUME COMPOSITION

The present invention relates to novel perfume compositions comprising a mixture of fragrant materials in a physiologically acceptable carrier comprising a mixture of polydimethylsiloxanes, characterized in that the said mixture of polydimethylsiloxanes consists of hexamethyldisiloxane and octamethyltrisiloxane in a hexamethyldisiloxane to octamethyltrisiloxane weight ratio ranging from 30:70 to 70:30.

The perfume compositions usually comprise a mixture of fragrant materials having a vapour pressure less than atmospheric pressure at 25° C. and are generally liquid at 25° C., but sometimes also solid, in a physiologically acceptable medium based on ethanol and optionally water.

Ethanol constitutes a good solubilizing agent for perfuming ingredients, and additionally has the advantage of being inexpensive and of allowing the formulation of transparent compositions. On the other hand, it has the disadvantage of adversely affecting the olfactory characteristics of the perfuming ingredients, not only because of its potent odour but also because of its capacity to react, in the presence of water, with the perfuming ingredients and to thereby modify their odour and/or their colour. It is in addition capable of chemically reacting with atmospheric nitrogen oxides to form ozone, which constitutes, in this regard, a source of atmospheric pollution which efforts are being made to avoid. Finally, ethanol is an irritant and may be a source of tingling when it is applied to a sensitive or damaged skin, in particular after shaving.

Several attempts have therefore been made to replace ethanol in perfume compositions with other solvents not having the above disadvantages.

A first route consists in replacing ethanol with aqueous compositions containing hydrophilic solubilizing agents such as polyethoxylated hydrogenated castor oils. The compositions obtained contain high percentages of these solubilizing agents which may be irritating, foaming and may have a sticky effect on the skin. Another route consists in formulating perfume compositions in the form of micro- and nanoemulsions. The oily phase of these emulsions, containing the perfuming ingredients, is however limited in quantity so as not to destabilize the emulsion, which reduces the perfuming effect of these compositions. Moreover, the presence of water in a large quantity is capable of causing degradation of the perfuming ingredients over time and therefore of adversely affecting the olfactory characteristics of the product.

Another solution further consisted in providing perfume compositions in which the ethanol is at least partially replaced by one or more volatile silicones which are linear— of the polydimethylsiloxane type—or cyclic. Such is the case in the document WO 99/01106 which discloses perfume compositions intended for impregnating textiles or nonwoven fabrics. The document U.S. Pat. No. 6,432,912 also discloses a perfume composition containing these volatile silicones, optionally used in the form of a mixture in order to adjust the rate of evaporation of the carrier, and which are combined with cosolvents such as esters optionally combined with diesters.

However, the applicant has now discovered, surprisingly, that by choosing a particular combination of silicone compounds not described in the prior art, it was possible to obtain a perfume composition whose rate of evaporation is close to that of ethanol and possessing a flash point greater than or equal to 0° C., preferably greater than or equal to 10° C.

The subject of the present invention is therefore a perfume composition comprising a mixture of fragrant materials in a physiologically acceptable carrier comprising a mixture of polydimethylsiloxanes, characterized in that the said mixture of polydimethylsiloxanes consists of hexamethyldisiloxane and octamethyltrisiloxane in a hexamethyldisiloxane to octamethyltrisiloxane weight ratio ranging from 30:70 to 70:30.

Advantageously, the hexamethyldisiloxane to octamethyltrisiloxane weight ratio ranges from 30:70 to 40:60. More preferably, the polydimethylsiloxane mixture contains 30% by weight of hexamethyldisiloxane and 70% by weight of octamethyltrisiloxane.

The polydimethylsiloxanes according to the invention are available in particular from the company DOW CORNING under the trade name Dow Corning Fluid 200 0.65 cst and 1 cst, from the company RHODIA under the trade name Silbione Huile 70041 0.65 D, from the company WACKER under the trade name Belsil DM 0.65 and from the company GE BAYER SILICONES under the trade name hexamethyldisiloxan.

The fragrant materials contained in the perfume composition according to the invention are compounds which are customarily used by perfumers and they are described in particular in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

They may be natural products (essential oils, absolutes, resinoids, resins, concretes) and/or synthetic products (hydrocarbons, alcohols, aldehydes, ketones, ethers, acids, esters, acetals, ketals, nitriles, saturated or unsaturated, aliphatic or cyclic).

Examples of essential oils comprise essential oils of lemon, orange, anise, bergamot, rose, geranium, ginger, neroli, basil, rosemary, cardamom, camphor, cedar, camomile, sandalwood, sage, and mixtures thereof, without this list being limiting.

Examples of other fragrant compounds are in particular: geraniol, geranyl acetate, farnesol, borneol, bornyl acetate, linalol, linalyl acetate, linalyl propionate, linalyl butyrate, tetrahydrolinalol, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, alpha-hexylcinnamaldehyde, 2-methyl-3-(p-tert-butylphenyl)-propanal, 2-methyl-3-(p-isopropylphenyl)propanal, 3-(p-tert-butylphenyl)propanal, 2,4-dimethylcyclohex-3-enylcarboxaldehyde, tricyclodecenyl acetate, tricyclo-decenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetra-hydropyran, 3-carboxymethyl-2-pentylcyclopentane, 2-n-heptylcyclopentanone, 3-methyl-2-pentyl-2-cyclo-pentenone, menthone, carvone, tagetone, geranylacetone, n-decanal, n-dodecanal, 9-decen-1-ol, phenoxyethyl isobutyrate, phenylacetaldehyde dimethyl acetal, phenylacetaldehyde diethyl acetal, geranonitrile, citronellonitrile, cedryl acetate, 3-isocamphylcyclo-hexanol, cedryl methyl ether, isolongifolanone, aubepine nitrile, aubepine, heliotropine, coumarin, eugenol, vanillin, diphenyl oxide, citral, citronellal, hydroxycitronellal, damascone, ionones,-methylionones, isomethylionones, solanone, irones, cis-3-hexenol and its esters, indan musks, tetralin musks, isochroman musks, macrocyclic ketones, macrolactone musks, ethylene brassylate and mixtures thereof.

The composition according to the present invention usually contains from 2 to 60% by weight, and preferably from 5 to 40% by weight, of fragrant materials. It additionally contains a sufficient quantity of polydimethylsiloxanes to solubilize the fragrant materials, and preferably from 20 to 99% by weight of polydimethylsiloxanes, relative to the total weight of the composition.

The perfume composition according to the invention also generally comprises solvents, adjuvants or additives commonly used in the perfume sector which do not adversely affect the desired olfactory effect. Preferably, however, this composition does not contain an ester of a $C_4$-$C_{10}$ acid and of a $C_4$-$C_{15}$ alcohol.

This perfume composition may constitute an eau de Cologne, an eau de toilette, a perfume or an aftershave lotion.

Depending on its flash point, it may be packaged in an atomizer or possibly in an aerosol device. In the latter case, the composition according to the invention additionally contains a propellant gas such as dimethyl ether, propane, n-butane, isobutane, pentane, trichlorofluoromethane, dichlorodifluoro-methane, chlorodifluoromethane, 1,1,1,2-tetrafluoroethane, chloropentafluoroethane, 1-chloro-1,1-difluoroethane, 1,1-difluoroethane, and mixtures thereof. Dimethyl ether, isobutane and 1,1,1,2-tetrafluoroethane are preferably used, and preferably isobutane.

The invention will now be illustrated with the following nonlimiting examples. In these examples, the quantities are indicated as a percentage by weight.

EXAMPLES

Example 1

Comparative Study of the Properties of Various Mixtures of Silicones

Various mixtures of silicones were tested in order to evaluate, on the one hand, their rate of evaporation and, on the other hand, the flash point of a composition comprising these mixtures in combination with a perfume.

a) Protocols
Flash Point

The test composition is heated in a closed cup of standard sizes at a temperature about 3° C. less than the presumed flash point, for 60 seconds. Next, a flame of standard size is introduced into the vapours in the cup through a sliding opening. The test is repeated in 1° C. steps. The lowest temperature at which ignition occurs is noted as being the flash point.

The test is carried out in a SETAFLASH apparatus according to the ISO 3679 standard.

Rate of Evaporation 15 g of solvent to be tested are introduced into a crystallizing dish (diameter: 7 cm) placed on a balance which is in a chamber of about 0.3 m³ whose temperature (25° C.) and humidity (relative humidity: 50%) are regulated.

The solvent is allowed to evaporate freely, without stirring, while ventilating using a ventilator (PAPST-MOTOREN, reference 8550 N, revolving at 2700 revolutions/min) placed vertically above the crystallizing dish containing the solvent, the blades being directed towards the crystallizing dish and at a distance of 20 cm relative to the base thereof.

The mass of solvent remaining in the crystallizing dish is measured at regular intervals during the first thirty minutes of evaporation. The rate of evaporation is expressed in mg of solvent evaporated per unit of surface area ($cm^2$) and per unit of time (minute).

b) Results

The table below groups together the results obtained for various combinations of volatile silicones, in variable weight ratios. In this table:

| Mixture of silicones | | Rate of evaporation (mg/cm²/min) | Flash point* (° C.) |
| --- | --- | --- | --- |
| 30/70 | L2/L3 | 4.23 | +11 |
|  | L2/L4 | 3.25 | — |
|  | L2/L5 | 3.39 | — |
| 40/60 | L2/L3 | 5.39 | — |
| 55/45 | L2/L3 | 6.98 | +2 |
| 60/40 | L2/L3 | — | +2 |
| 70/30 | L2/L3 | 8.97 | 0 |
|  | L2/L5 | 7.77 | −1 |

L2 denotes hexamethyldisiloxane
L3 denotes octmethyltrisiloxane
L4 denotes decamethyltetrasiloxane
L5 denotes dodecamethylpentasiloxane
*Compositions comprising from 12 to 17.7% by weight of perfume extract in the mixture of silicones.

By way of comparison, the rate of evaporation of ethanol, measured under the same conditions, is 5.13 mg/cm²/min. The flash point of a composition comprising 12% by weight of perfume extract in ethanol is 16° C. That of a composition comprising 12% by weight of perfume extract in hexamethyldisiloxane is −5° C.

As is evident from this table, the mixtures of silicones consisting of the silicone L2 combined with another silicone chosen from the silicones L4 and L5, in weight ratios ranging from 70:30 to 30:70, do not always make it possible to obtain compositions having a flash point greater than 0° C. and a volatility at least equal to 4 mg/cm²/min, unlike the mixture of silicones according to the invention.

Example 2

Perfume Compositions

The compositions below were prepared in a conventional manner for persons skilled in the art.

| Composition A | |
| --- | --- |
| Perfume extract "Noa" | 12% |
| Hexamethyldisiloxane | 48.4% |
| Octamethyltrisiloxane | 39.6% |
| Composition B | |
| Perfume extract "Emporio White" | 17.7% |
| Hexamethyldisiloxane | 24.7% |
| Octamethyltrisiloxane | 57.6% |

The invention claimed is:
1. A perfume composition comprising:
at least one fragrant material; and
a physiologically acceptable carrier, with which the at least one fragrant material is mixed;
wherein:
the carrier comprises a mixture of polydimethylsiloxanes;
the mixture of polydimethylsiloxanes comprises hexamethyldisiloxane and octamethyltrisiloxane;

a weight ratio of hexamethyldisiloxane to octamethyltrisiloxane is from 30:70 to 70:30; and the composition does not comprise an ester of a $C_4$-$C_{10}$ acid and a $C_4$-$C_{15}$ alcohol.

2. The composition according to claim 1, wherein the hexamethyldisiloxane to octamethyltrisiloxane weight ratio ranges from 30:70 to 40:60.

3. The composition according to claim 1, wherein the mixture of polydimethylsiloxanes comprises 30% by weight of hexamethyldisiloxane and 70% by weight of octamethyltrisiloxane.

4. The composition according to claim 1, wherein the composition comprises from 5 to 40% by weight of the at least one fragrant material.

5. The composition according to claim 1, wherein the composition comprises from 20 to 99% by weight of the mixture of polydimethylsiloxanes.

6. An aerosol device comprising the composition of claim 1 and a propellant gas.

7. The composition according to claim 2, wherein the composition comprises from 5 to 40% by weight of the at least one fragrant material.

8. The composition according to claim 3, wherein the composition comprises from 5 to 40% by weight of the at least one fragrant material.

9. The composition according to claim 2, wherein the composition comprises from 20 to 99% by weight of the mixture of polydimethylsiloxanes.

10. The composition according to claim 3, wherein the composition comprises from 20 to 99% by weight of the mixture of polydimethylsiloxanes.

11. The composition according to claim 4, wherein the composition comprises from 20 to 99% by weight of the mixture of polydimethylsiloxanes.

12. An aerosol device comprising the composition of claim 2 and a propellant gas.

13. An aerosol device comprising the composition of claim 3 and a propellant gas.

14. An aerosol device comprising the composition of claim 4 and a propellant gas.

15. An aerosol device comprising the composition of claim 5 and a propellant gas.

* * * * *